United States Patent [19]

Brisson et al.

[11] Patent Number: 4,495,944
[45] Date of Patent: Jan. 29, 1985

[54] INHALATION THERAPY APPARATUS

[75] Inventors: Alfred Brisson; Christopher Nowacki, both of Arlington Hts., Ill.

[73] Assignee: Trutek Research, Inc., Arlington Hts., Ill.

[21] Appl. No.: 464,219

[22] Filed: Feb. 7, 1983

[51] Int. Cl.³ .................................................. A61B 5/08
[52] U.S. Cl. ..................................... 128/725; 128/716; 272/99; 340/62; 340/815.12; 340/611
[58] Field of Search ................. 128/716, 720, 725–729, 128/205.23; 272/99 R; 340/62, 54, 815.12, 573, 691, 611, 815.01

[56] References Cited

U.S. PATENT DOCUMENTS

| 1,010,412 | 12/1911 | Butler ........................... 340/62 |
| 4,170,225 | 10/1979 | Criglar et al. .................. 128/732 |
| 4,223,297 | 9/1980 | Nomura et al. ................. 340/62 |
| 4,231,375 | 11/1980 | Boehringer et al. ............ 128/725 |
| 4,241,739 | 12/1980 | Elson .............................. 128/725 |
| 4,391,283 | 7/1983 | Sharpless et al. ............... 272/99 |

FOREIGN PATENT DOCUMENTS 2237196  2/1975  France .................................. 340/62

OTHER PUBLICATIONS

Cunningham et al., "Performance Indicator for Subject Motivation in Respiratory Tests", Med. & Biol. Eng. & Comput., (1979), 17, 061–067.

Primary Examiner—Henry J. Recla
Attorney, Agent, or Firm—Trexler, Bushnell & Wolters, Ltd.

[57] ABSTRACT

Inhalation therapy apparatus comprises a mouthpiece through which air is to be inhaled and provides a pneumatic signal related to the volume of air inhaled. The pneumatic signal is transduced to electrical information and provides visual indicia to be observed by the patient to encourage the patient's performance. One row of lights indicates a desired level of inhalation to be attained, while a parallel row of lights indicates the inhalation actually attained. A step wise visual configuration also is provided encouraging the patient to increase his inhalation step by step. A visual display is also provided of the total number of attempts or inhalations, and also the number of times that the desired volume is attained.

4 Claims, 5 Drawing Figures

U.S. Patent      Jan. 29, 1985      4,495,944
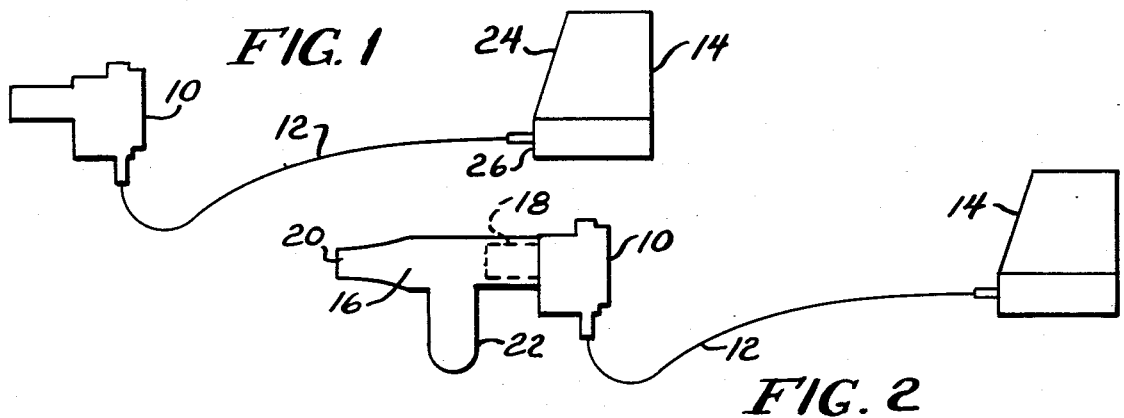
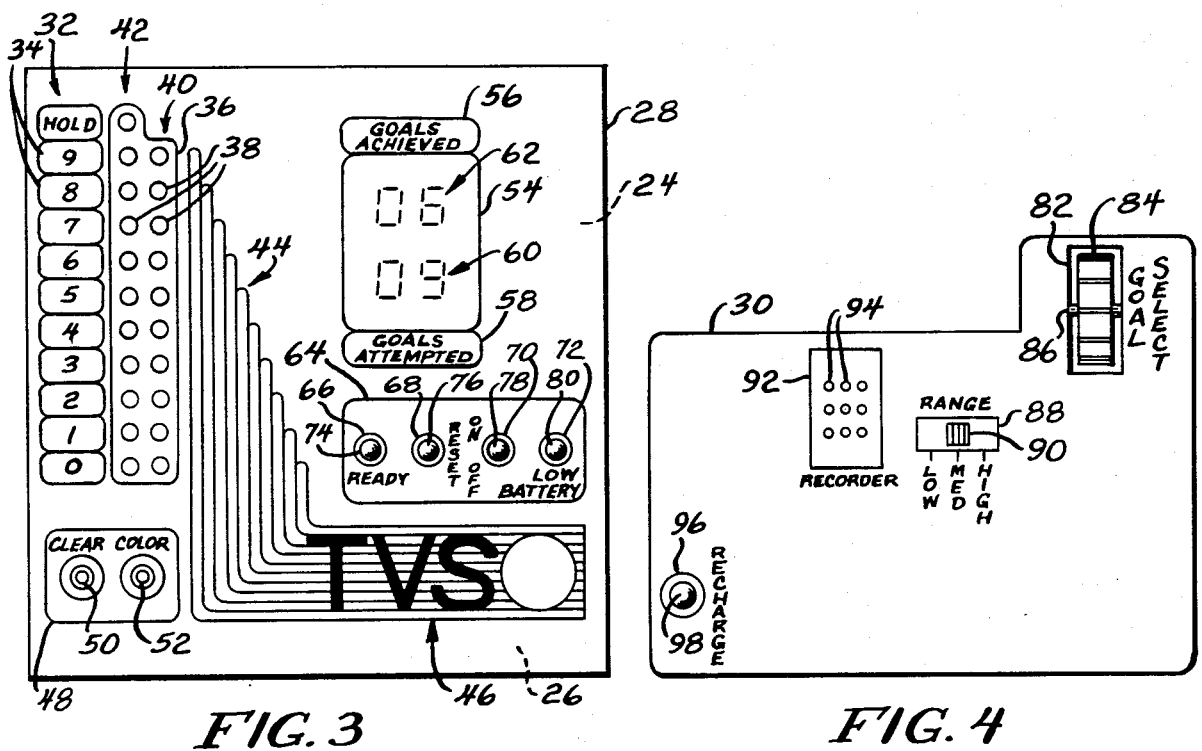
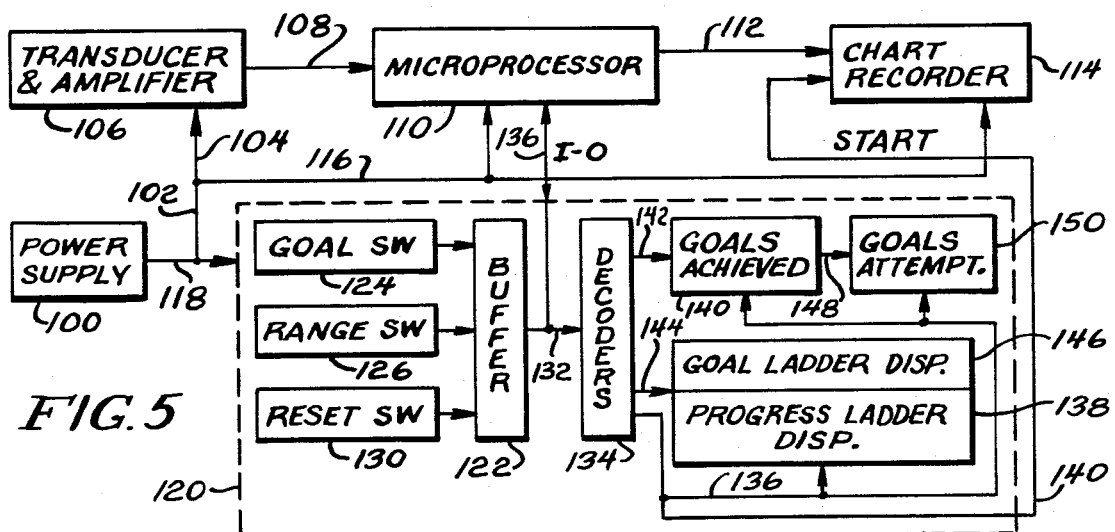

INHALATION THERAPY APPARATUS

RELATED INVENTIONS

The present invention preferably incorporates the Inhalation Valve of our co-pending application Ser. No. 394,403, filed July 1, 1982 and the electronic circuitry of our copending application for Inhalation Transducer Circuit, Ser. No. 415,735, filed Sept. 7, 1982. The disclosures of both of said applications are hereby incorporated by reference. Both of said co-pending applications and the present application are signed to Trutek Research, Inc. of Arlington Heights, Illinois.

BACKGROUND OF THE INVENTION

In the treatment of patients suffering from various respiratory problems, either acute or chronic in nature, involving the lungs, bronchia, etc., it is often necessary to test the breathing capacity of the patient. The inhalation valve of our prior application Ser. No. 394,403 serves admirably for such purpose as does the transducer circuit of our application Ser. No. 415,735. However, we have found that better results and better breathing efficiency can be attained when definite goals are set for the patient, which goals can be visualized, and wherein the patient can visually ascertain when he has reached a goal or approached it.

OBJECT AND SUMMARY OF THE PRESENT INVENTION

It is an object of the present invention to provide an inhalation valve therapy apparatus in which goals for breathing capacity can be pre-set and visualized for the patient, and wherein a patient can personally see whether he attains the goal, or just how close he comes to attainment.

It is a further object of the present invention to provide inhalation therapy apparatus utilizing a disposable or throw away mouthpiece, wherein the patient can personally visualize his progress.

In attaining the foregoing and other and further objects we have provided an inhalation therapy apparatus having a disposable or throw away mouthpiece. Knowing that no one previously has utilized a particular mouthpiece or will ever use it again, enchances the patient's feeling of well being, and tends to maximize his breathing capacity.

A mouthpiece of the present invention is connected by one or two flexible pneumatic tubes of small diameter and light weight to an electronic module having various advantages for the patient. The electronic module has provision for pre-selecting a goal which the patient will hope to attain. The goal can be set by the patient personally, or the patient can participate in the selection. A visual display is made of the goal as set, and when the patient inhales a visual display is made of the level of attainment, immediately adjacent to the visual display of the goal. Since the patient can see the side by side comparison, there is a greater incentive for him to try harder, and thereby to inhale more deeply than he otherwise would be likely to do without the visual incentive. The electronic module further provides a visual recordation of the goals attempted and the number of times the goal has been achieved.

The mouthpiece or inhalation valve of the present invention may further be used in conjunction with a commercial nebulizer to introduce medication to the patient's bronchia and lungs as an incident to the testing of his inhalation.

THE DRAWINGS

The present invention will best be understood with reference to the ensuing specification when taken in connection with the accompanying drawings wherein FIG. 1 comprises a somewhat schematic side view of inhalation therapy apparatus constructed in accordance with the present invention.

FIG. 2 is a view similar to FIG. 1 showing the invention as used in combination with a commercial nebulizer.

FIG. 3 is a front view of the housing of the electronic module.

FIG. 4 is a rear view thereof and

FIG. 5 is an electronic block diagram illustrating the electronic circuits of the present invention.

DETAILED DESCRIPTION OF THE ILLUSTRATED EMBODIMENT

Turning now in greater particularity to the drawings, and first to FIG. 2 there is shown rather generally, an inhalation valve 10 which may be the same as the inhalation valve shown in our co-pending application Ser. No. 394,403. It may also be a somewhat simpler valve without the valve flap, but simply a pitot tube or venturi. With such simpler valve or mouthpiece the patient would not exhale through the mouthpiece, but would remove the valve or mouthpiece 10 for exhalation. The valve or mouthpiece 10 is connected by pneumatic tubing 12 to an electronic module 14. This module incorporates the electronics disclosed in our co-pending application Ser. No. 415,735, plus additional circuitry as will be set forth hereinafter. The pneumatic tubing 12 may comprise two separate tubes, preferably color coded, to provide a differential pressure to the electronic module 14. However, it is possible to use only a single tube, and to plug the corresponding connections in the mouthpiece or valve 10 and in the electronic module 14. In this case, a differential pressure would still be utilized, but the differential would be relative to ambient pressure.

Although the primary purpose of the present invention is to provide apparatus for testing breathing, specifically inhalation capacity, the invention is also usable for introducing medication into the patient's bronchia and lungs. As shown in FIG. 2 a commercial nebulizer 16 is placed over the extending mouthpiece portion 18 of the valve or mouthpiece 10, the nebulizer having itself a mouthpiece 20 for insertion in the patient's mouth. A depending vial 22 holds the liquid medication and the necessary aspiration tube. As will be understood by those skilled in the art the liquid medication is broken up in a venturi to form small particles larger than 30 microns in size. This is distinguished from an aerosol dispersal in which the particles are smaller than 30 microns.

Returning now to FIG. 1, the electronic module 14 includes a housing having an inclined upper face 24 and a vertical lower face 26. Information is displayed on the faces 24 and 26 indicative of the operation of the electronic module as controlled by the valve or mouthpiece 10, and providing a visual inspiration for the patient to do his best.

To provide a display visable by the patient a translucent decal 28 (FIG. 3) is provided which is adhered to the front faces 24 and 26 of the electronic module and which cooperates with lights or fittings thereon. An opaque decal 30 (FIG. 4) is adhered to the back surface of the electronic module housing, and more will be said about this later.

Returning to FIG. 3, along the left margin of the decal 28 there is a column of indicia 32, comprising horizontal rectangles 34 bearing numerals 0 through 9 from the bottom to near the top of the column, topped by a rectangle labeled "HOLD". Immediately to the right of the column 32 there is a vertical generally rectangular cutout 36 in the decal exposing two columns of lights 38. The right column 40 has ten lights horizontally aligned with the 0 through 9 rectangles, while the left column 42 is one light longer, having lights horizontally aligned with the rectangles 0 through 9, and with one extra light at the top horizontally aligned with the rectangle "HOLD".

Immediately to the right of the cutout 36 is a series of ten vertical columns 44 of decreasing height. The first column has its top opposite the rectangle 9, the second has its top opposite the rectangle 8, and so forth down through the tenth column which is opposite the rectangle 0. The columns make right angle bends at the bottom ends thereof to form horizontal rows 46 in a decorative pattern.

To the left of the columns 44 and below the rectangles 34 and cutout 36 there is a rectangle 48 having two pneumatic fittings 50 and 52 therein. The fitting 50 is labeled "Clear", while the fitting 52 is labeled "Color". When a tube or conduit pneumatic tubing 12 is utilized between the valve or mouthpiece 10 and the pneumatic module 14, the two tubes are respectively cleared and colored, and thus are coded for connection to the pneumatic fittings 50 and 52, respectively.

Toward the upper right hand corner of the decal 28 there is provided a rectangle 54 which is colored, preferably red, for cooperation with red light emitting diodes of the like arranged in the unusual seven segment array for indicating various numerals soon to be indicated. Immediately above the rectangle is a small, horizontally disposed bar or rectangle 56 labeled "Goals Achieved." A similar bar or rectangle 58 immediately underlies the rectangle 54 and is labeled "Goals Attempted." Counter devices are provided in the electronic module 14, and numerals are provided at 60 behind the rectangle 54 to indicate the number of inhalation cycles or goals attempted. Above that is a numeral display 62 behind the rectangle 54 which indicates the number of goals achieved, i.e., the number of times that the inhalation has been up to the pre-selected standard.

Below the rectangle 54 and spaced from the bar or rectangle 58, and immediately above the rows 46 and to the right of the columns 44 is a rectangle 64. The rectangle 64 is horizontally disposed, and is provided with four cutouts 66, 68, 70 and 72. The first cutout 66 displays a lamp 74 which becomes illuminated after the apparatus has been turned on, and when it is ready. This lamp is labeled "Ready." The next cutout 68 is provided with a push button 76 labeled "Reset" for resetting the light columns 38 to 0 and for resetting the goals attempted and goals achieved.

The next cutout 70 is provided with an on-off push button 78 for turning the apparatus on and off. The fourth cutout 72 is provided with a lamp 80 which becomes illuminated to indicate a low battery condition, and is so labeled. The lamps 74 and 80 preferably are light emitting diodes for low power consumption.

The back label or decal 30 is provided near its upper right hand corner with a cutout 82 displaying therein slightly less than ½ of a serrated wheel 84 which extends part way therefrom, and which is fixed on a horizontal shaft 86 for rotation by the thumb or fingers. This wheel is labeled "Goal Select" and is movable to select the level of inhalation to be illuminated by the right hand column of lamps 38. The wheel is connected to suitable electronic devices to produce a digital code indicating its position, and hence to operate through the electronic module to eliminate the right column of lamps 38.

Slightly to the right and above the horizontal midline, there is a horizontally disposed rectangular cutout 88 having a label "Range" above it, and three index marks with respective labels "Low", "Med", and "High". The operating member 90 of a slide switch extends through the cutout 88 for setting the range to be used for a given patient. For example, with a patient of low lung capacity the range would be set at "Low", and this would cover all of the scale of 0 to 9 of the lamps 38. In accordance with one example this would correspond to an inhale volume of 1.9 liters. On the other hand, for a patient of rather considerable lung capacity the range would be set to "High", and again in a particular example this would correspond to 5.4 liters of inhaled air. The "Med" corresponds to medium, and would be at an intermediate volume of inhaled air. In any event, the range selection is to permit use of most of the lights at levels 0 through 9 for any given patient, whether he have excellent lung capacity or poor lung capacity.

Just to the left of the range cutout 88 there is a cutout 92 providing access for a recorder connection indicated by a plurality of pins 94 whereby the apparatus may operate a chart recorder to provide a permanent record of the inhalations made by a patient.

At the lower left of the decal 30 there is provided a circular cutout 96 having an electrical connection 98 for recharge of the battery which operates the electronic module.

Turning now to FIG. 5 the electronic circuitry of the electronic module 14 is shown in black box form. There is a power supply 100 which comprises essentially a battery and the on-off switch 78. The power supply supplies power for the remainder of the circuitry. The battery preferably is of the rechargeable type, and preferably is selected from those commercially available.

Power from the power supply is connected through lines 102 and 104 to a transducer and amplifier 106. This transducer converts the pneumatic signal produced by the valve or mouthpiece 10 and tubing 12 to an electrical signal, and preferably is identical with that disclosed in our previously referenced co-pending application Ser. No. 415,735. This transducer and amplifier is connected at 108 to a microprocessor 110, as noted in the same co-pending application. Signals from the microprocessor are provided at 112 to drive a chart recorder 114, which is a commercially available part external to the electronic module 14, and connected at the pin connections 94 on the back of the housing.

The power supply is connected through the previously mentioned line or connection 102 and an additional line or connection 116 to the microprocessor and to the chart recorder. Power is also supplied through a line 118 to electronic circuits grouped at 120.

The electronic circuits 120 include a buffer 122 which preferably comprises a tri-state buffer, having connected to it the goal select switch 124 controlled by the thumb wheel 84, the range switch 126 controlled by the slider or operating member 90, and the reset switch 130 controlled by the reset push button 76. An output 132 from the buffer is connected to decoders 134, and also through an input-output line 136 to the microprocessor 110. These decoders are connected through a line 136 to a progress ladder display circuit 138 which causes lighting of an appropriate one of the lights or lamps 38 of the left column 42. The line 136 also leads to a "Goals Achieved" circuit 140 which also has a connection at 142 from the decoders, and determines the numeral that will appear at 62. A tap from the line 136 leads at 140 to the chart recorder 114 to start operation thereof.

Connection is made at 144 from the decoders to the progress ladder display circuit 138, and also to a goal ladder display circuit 146, the latter determining which of the lamps 38 in the column 40 will be illuminated. An output 148 from the goals achieved circuit 140 leads to a goals attempted circuit 150, which further is connected to the line 136. This circuit 150 determines the numeral that will appear at 60.

In order to use the present apparatus an estimate is made of a patient's breathing capacity, specifically inhalation, which may be based on past performance, or on an educated medical estimate. After the apparatus has been turned on by means of the push button switch 78, and following a short wait until the ready light 74 comes on, the proper range is selected by the slider 90, and the goal select wheel 84 is operated to cause illumination of one of the lights 38 in the column 40 to indicate the goal selected for the patient. The patient watches the display provided in connection with the label or decal 28 and various lights, and inhales through the valve or mouthpiece 10, either with or without the nebulizer 16. The lights in the column 42 sequentially light from the bottom up and the patient can watch the lights ascending in an effort to inhale sufficiently to illuminate the light 38 in the column 42 to match on the same level with the illuminated light in the column 40. If the patient is successful in achieving that level, he is psychologically rewarded by having the top light in the column 42 light. This light stays on for five seconds opposite the "HOLD" label and then extinguishes, advising the patient that he should exhale through the mouthpiece. (It will be understood that with a simple type valve without a flap for sealing off on exhalation it would be necessary for the patient to remove the mouthpiece from his mouth for exhalation. This is a natural tendency in any event, and no great inconvenience).

When a patient inhales the circuitry operates to indicate a goal attempted by the numerals 60. Obviously, for the first attempt the numeral 1 will be displayed. If the patient is successful in achieving the desired goal or level, then the numeral 1 also appears at 62. Successive inhalation efforts are made in the same fashion, and the goals attempted will continue to be displayed in increasing numerals at 60, while the goals achieved will be displayed at 62. The latter number may in the ideal case equal the former number, but typically will fall somewhat behind. Inhalation efforts may continue to the extent desired by the attending physician or inhalation therapist. The display is watched at all times by the patient, thus providing a psychological incentive for him to inhale more deeply than he might otherwise feel himself capable of, and his efforts, if successful, are met by a psychological reward as the lights illuminate.

It is also psychological stimulating for a patient to try to keep the goals achieved equal to or nearly as equal as possible to the goals attempted. The column display at 44 provides the patient with a psychological feeling of climbing a mountain, enhanced by the feeling of reaching the desired level when he can match the light in the column 42 with the chosen light in the column 40. In short, it has been found to be a marked psychological advantage for the patient to be able to observe and monitor his own progress, with the capability of increasing the desired goal level, and hence to increase the patient's breathing capacity over a period of time.

The capability of the apparatus of utilizing the nebulizer in combination therewith markedly enhances the utility of the present invention. The use of the chart recorder is advantageous in providing a permanent record for the physician, and also for an inhalation therapist.

We have made various modifications in the present apparatus which produce enhanced results, but which do not change the overall combination as heretofor disclosed and as hereinafter claimed. In accordance with such changes the chart recorder 114 is no longer used, but rather there is provided a digital printer interface. At the end of each inhalation information is printed out as to status, inspiratory effort and equivalent liters the goal switch setting (whether high or low), the range switch setting, goals achieved, and goals attempted. This provides an improved record which is easy to read and preferable to the chart recorder.

In accordance with the preceeding disclosure the goals achieved column will not read higher than the goals attempted column, but will only match it. In accordance with a modification of the present invention the goals achieved can pass the goals set. For example, a goal of 5 can be set, and a readout can be provided for the actual goal achieved, for example 8. A switch is provided to choose whether the goals achieved will stop at the goal set, or will go to the actual goal achieved in each instance.

As heretofor disclosed the columns 40 and 42 of colored lights 38 indicate volume. In accordance with a modification these lights are used to indicate flow rate, from 0 to 60 liters per minute. This provides an instantaneous update of inspiratory flow and encourages the patient to maintain the desired flow rate. The two digit goals achieved display will continue to display the goals achieved, but the two digit goals attempted display will now display the volume goal during the resting period and the instantaneous inspired volume during the inhalation attempt. This volume goal is set using a switch on the rear of the unit. The flow goal as displayed on the light row is also set using a switch on the rear of the unit.

In order to attain the modifications as discussed it is only necessary to re-program the microprocessor, and this can readily be accomplished by any skilled programmer.

The specific examples of the invention as herein shown and described are for illustrative purposes only. Various changes will no doubt occur to those skilled in the art and will be understood as forming part of the present invention insofar as they fall within the spirit and scope of the appended claims.

The invention is claimed as follows:

1. Inhalation therapy apparatus comprising a mouthpiece for insertion in patient's mouth for inhalation therethrough and having pneumatic means producing a pneumatic signal corresponding to the volume of air inhaled, and an electric module pneumatically interconnected with said mouthpiece, said module comprising means for converting said pneumatic signal to electrical information, and display means visible to said patient and comprising means indicating a desired inhalation volume, means adjacent to said desired inhalation volme indicating means for indicating the volume of inhalation attained, said indicating means comprising a pair of parallel adjacent rows of light, said rows being oriented on said module in a vertical rectilinear manner with the lights in one row being horizontally aligned with the lights in the other row, and further including means representing a stair step arrangement with each step respectively being aligned with a pair of lights, one in each of said rows.

2. Inhalation therapy apparatus comprising a mouthpiece for insertion in patient's mouth for inhalation therethrough and having pneumatic means producing a pneumatic signal corresponding to the volume of air inhaled, and an electronic module pneumatically interconnected with said mouthpiece, said module comprising means for converting said pneumatic signal to electrical information, and display means visible to said patient and comprising means indicating a desired inhalation volume, means adjacent to said desired inhalation volume indicating means for indicating the volume of inhalation attained, means providing a visual indication of the inhalation attempts, means providing a visual indication of the number of times the desired inhalation volume is attained, said indicating means comprising a pair of parallel adjacent rows of lights, said rows being oriented on said module in a vertical rectilinear manner with the lights in one row being horizontally aligned with the lights in the other row, and further including means representing a stair step arrangement with each step respectively being aligned with a pair of lights, one in each of said rows.

3. Inhalation therapy apparatus comprising a mouthpiece for insertion in a patient's mouth for inhalation therethrough, means connected to said mouthpiece for providing an electrical signal related to the volume of air inhaled therethrough, and display means visable to a patient and including a first row of lights respectively illuminable to indicate a desired volume of inhalation, manually operable means for selectively illuminating one light of said first row of lights as a reference of desired inhalation volume, a second row of lights parallel to said first row of lights, each light of said second row of lights being opposite to a respective light of said first row and respectively illuminable to indicate the actual volume inhaled, and means interconnecting said electrical signal providing means and said second row of lights to successively control the illumination thereof in response to the volume of air inhaled, whereby the successive illumination of said second row of lights can be compared to the selected illuminated light of said first row of lights.

4. Apparatus as set forth in claim 3 wherein said second row of lights has one additional light illuminable to indicate that the inhaled volume attained is at least equal to the desired volume.

* * * * *